United States Patent [19]

Raheja et al.

[11] Patent Number: 5,453,435
[45] Date of Patent: Sep. 26, 1995

[54] PRESERVATIVE SYSTEM FOR CONTACT LENS SOLUTIONS

[75] Inventors: Manohar K. Raheja, North Andover; Stanley J. Wrobel, Andover, both of Mass.

[73] Assignee: Polymer Technology Corporation, Wilmington, Mass.

[21] Appl. No.: 180,632

[22] Filed: Jan. 13, 1994

Related U.S. Application Data

[63] Continuation of Ser. No. 1,486, Jan. 7, 1993, abandoned.

[51] Int. Cl.$^6$ .................... A61K 31/415; A61K 31/135
[52] U.S. Cl. .................... 514/402; 514/653; 514/912
[58] Field of Search .................... 514/402, 653, 514/912

[56] References Cited

U.S. PATENT DOCUMENTS

| | | | |
|---|---|---|---|
| Re. 29,693 | 7/1978 | Phares | 424/326 |
| 4,354,952 | 10/1982 | Riedhammer et al. | 252/106 |
| 4,537,746 | 8/1985 | Ogunbiyi et al. | 422/28 |
| 4,587,266 | 5/1986 | Verdicchio | 514/635 |
| 4,758,595 | 7/1988 | Ogunbiyi et al. | 514/635 |

FOREIGN PATENT DOCUMENTS

92/11876  7/1992  WIPO.

OTHER PUBLICATIONS

"Trans–Epithelial Permeability of Fluorescein In Vitro Toxicology", vol. 6, 1988, pp.: 271–283 (Mary ann Liebert, Inc. Publishers, New York).

*Primary Examiner*—Zohreh Fay
*Attorney, Agent, or Firm*—Craig E. Larson; Denis A. Polyn

[57]  ABSTRACT

A preservative system for ophthalmic solutions, particularly contact lens solutions, comprises:
  (a) chlorhexidine or a water-soluble salt thereof; and
  (b) polyhexamethylene biguanide or a water-soluble salt thereof.

22 Claims, No Drawings

PRESERVATIVE SYSTEM FOR CONTACT LENS SOLUTIONS

This is a continuation of application Ser. No. 08/001,486 filed on Jan. 7, 1993, now abandoned.

BACKGROUND OF THE INVENTION

This invention relates to an improved preservative system for ophthalmic solutions, especially solutions for the care of contact lenses. The solutions contain as the preservative chlorhexidine and polyhexamethylene biguanide, or salts thereof.

Since ophthalmic solutions, including solutions used for the care of contact lenses, either directly or indirectly come into contact with the eye, it is important that the solutions do not become contaminated with microorganisms. Conventionally, such solutions are packaged under sterile conditions, and many solutions incorporate an antimicrobial agent as a preservative for inhibiting growth of microorganisms which may contaminate the solution. For ophthalmic solutions used for contact lens care, the antimicrobial agent often also serves to disinfect and/or preserve contact lenses when rinsed or immersed in the solution.

A challenge is to develop preservative systems which not only have a wide spectrum of antimicrobial activity but which also are more suitable for ophthalmic applications and less irritating to the eye. Preservatives provide desired antibacterial effects, but preservatives are, by their nature, irritating to the eye. Thus, while antimicrobial efficacy of a solution could be improved by merely increasing the amount of the active agent, the potential for eye irritation increases as the concentration of the active agent is increased. Conversely, decreasing the concentration of the antimicrobial agent could lessen eye irritation, but antimicrobial efficacy would decrease.

SUMMARY OF THE INVENTION

The present invention relates to improved ophthalmic solutions which comprise an antimicrobially effective amount of a preservative, wherein the preservative comprises: (a) chlorhexidine or a water-soluble salt thereof; and (b) polyhexamethylene biguanide or a water-soluble salt thereof. Additionally, the invention relates to methods of treating contact lenses, such as methods of disinfecting contact lenses, which employ an ophthalmic solution comprising the antimicrobial agent.

DETAILED DESCRIPTION OF THE INVENTION

The first component of the preservative system is a compound selected from the group consisting of chlorhexidine (1,1'-hexamethylene-bis[5-(p-chlorophenyl) biguanide]) and water soluble salts thereof. Suitable salts include the gluconate, isethionate (2-hydroxyethanesulfonate), formate, acetate, glutamate, succinamate, monodiglycollate, dimethanesulfonate, lactate, diisobutyrate and glucoheptonanate salts. A preferred material is chlorhexidine gluconate (available from ICI Americas, Inc., Wilmington, Delaware, USA).

The second component of the preservative system is a compound selected from the group consisting of polyhexamethylene biguanide (a polymer of hexamethylene biguanide, also referred to as polyaminopropyl biguanide) and water-soluble salts thereof. The polyhexamethylene biguanides include repeating units of the formula:

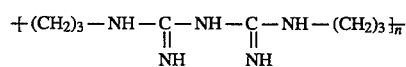

wherein n is 2 to 500, and include biguanides represented by formula (I):

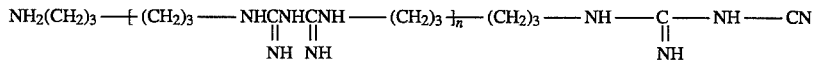

wherein n is 2 to 500, and water-soluble salts thereof.

Preferred polyhexamethylene biguanides include lower molecular weight oligomers, including biguanides of formula (I) wherein n averages between 4 to 12. Suitable salts include the hydrochloride, borate, acetate, gluconate, sulfonate, tartrate and citrate salts. A more preferred material is the polyhexamethylene biguanide hydrochloride available under the trade name Cosmocil CQ (IcI Americas Inc., Wilmington, De., USA).

Applicants have discovered that the preservative system of this invention provides desired antimicrobial efficacy with relatively low amounts of chlorhexidine and polyhexamethylene biguanide, thus reducing the potential for eye irritation from these preservatives.

The preservative system is employed in ophthalmic solutions in an antimicrobially effective amount. As used herein, the term "ophthalmic solution" denotes an aqueous solution intended for application in the eye, including solutions for the care of contact lenses. Contact lens solutions include solutions for the care of soft hydrogel lenses and hard lenses including rigid gas permeable (RGP) lenses. Such solutions for the care of contact lenses include saline solutions, cleaning solutions, disinfection solutions, conditioning solutions, soaking solutions and rinsing solutions.

The term "preservative" or "preservative system" denotes the agents included in the ophthalmic solutions for the purpose of inhibiting the growth of microorganisms in the product, thereby helping to maintain sterility during use. Additionally, the term "antimicrobial agent" is used herein to denote a specific active agent which provides the antimicrobial efficacy.

The term "antimicrobially effective amount" denotes an amount which is effective to at least inhibit growth of microorganisms in the solution. Preferably, the amount of antimicrobial agents is sufficient to disinfect the solution by killing microorganisms therein according to international preservative efficacy requirements for ophthalmic solutions, including FDA and British Pharmacopeia requirements.

Generally, the ophthalmic solutions include about 0.0005 to about 0.0060 weight percent of the chlorhexidine component, and about 0.00001 to about 0.0015 weight percent of the polyhexamethylene biguanide component. According to preferred embodiments, the ophthalmic solutions include no more than about 0.0040 weight percent of the chlorhexidine component, and no more than about 0.0010 weight percent of the polyhexamethylene biguanide, in order to minimize eye irritation; preferably, the solutions include at least about 0.0020 weight percent of the chlorhexidine component and at least about 0.0001 weight percent of the hexamethylene biguanide component, in order to ensure adequate antimicrobial efficacy.

Although the optimum amounts of the antimicrobial agents may vary among specific ophthalmic solutions, specific amounts of each antimicrobial agent can be readily determined by a person of ordinary skill in the art following testing methods known in the art.

The ophthalmic solutions may include other components known in the art.

Preferably, the solutions further include a sequestering agent (or chelating agent) which is normally present at about 0.025 to about 2.0 weight percent. Examples of preferred sequestering agents include ethylenediaminetetraacetic acid (EDTA) and its salts, with the disodium salt (disodium edetate) being especially preferred.

Generally, the solutions include buffering agents for buffering or adjusting pH of the solution, and/or tonicity adjusting agents for adjusting the tonicity of the solution. Representative buffering agents include: alkali metal salts such as potassium or sodium carbonates, acetates, borates, phosphates, citrates and hydroxides; and weak acids such as acetic, boric and phosphoric acids. Generally, buffering agents are present at about 0.01 to about 2.5 weight percent. Representative tonicity adjusting agents include: sodium and potassium chloride, and those materials listed as buffering agents. The tonicity agents may be employed in an amount effective to adjust the osmotic value of the final solution to more closely resemble that of human tears, generally at about 0.01 to about 2.5 weight percent.

Additionally, the solutions may include wetting agents or viscosity modifiers. Representative wetting agents and viscosity modifiers include: cellulose derivatives, such as cationic cellulosic polymers, hydroxypropyl methylcellulose, hydroxyethylcellulose and methylcellulose; polyols, such as polyethylene glycol, glycerine and polyethylene oxide (PEO) containing polymers; polyvinyl alcohol; and polyvinyl pyrrolidone. Such additives may be used in a wide range of concentrations as is known in the art.

The following examples further illustrate preferred embodiments of the present invention.

EXAMPLE 1

Three contact lens solutions for conditioning and disinfecting contact lenses were prepared by mixing the components listed in Table 1. It is noted that Solution A includes the preservative system of this invention, whereas Solutions B and C were prepared for comparative purposes.

TABLE I

| Component (Wt. %) | Soln A | Soln B | Soln C |
|---|---|---|---|
| Chlorhexidine Gluconate | 0.0030 | 0.0060 | — |
| Polyhexamethylene Biguanide HCl* | 0.0005 | — | 0.0015 |
| Disodium Edetate | 0.050 | 0.050 | 0.050 |
| Phosphate Buffer | 0.335 | 0.335 | 0.335 |
| Tonicity Adjusting Agents | 0.950 | 1.000 | 0.950 |
| Wetting Agents and/or Viscosity Modifiers | 1.200 | 1.095 | 0.670 |
| Purified Water | q.s. to 100 | q.s. to 100 | q.s. to 100 |

*Cosmocil CQ

The contact lens solutions from Table I were subjected to challenge tests to determine efficacy against various organisms. Samples of each solution were inoculated with the organisms at the concentrations shown in Table II. Viability was tested at various periods following initial inoculation as reported in Tables III, IV and V. In the tables, "TNTC" designates "too numerous to count".

TABLE II

| Organism | Inoculum (cfu/ml) |
|---|---|
| *Staphylococcus aureus* 6538 | $1.6 \times 10^6$ |
| adapted *Serratia marcescens* 48 | $1.5 \times 10^6$ |
| *Serratia marcescens* 48 | $2.1 \times 10^6$ |
| *Pesudomonas cedacia* 25416 | $4.4 \times 10^5$ |
| *Aspergillus niger* | $2.5 \times 10^5$ |
| *Pseudomanas aeruginosa* 9027 | $1.9 \times 10^6$ |

TABLE III

Solution A

| Organism | Viability (cfu/ml) | | | | |
|---|---|---|---|---|---|
| | 6 Hr | 1 day | 7 Day | 16 Day | 28 Day |
| S. aureus | $0 \times 10^1$ | $0 \times 10^1$ | $0 \times 10^1$ | $0 \times 10^1$ | $0 \times 10^1$ |
| ad. S. marcescens | $0 \times 10^1$ | $0 \times 10^1$ | $0 \times 10^1$ | $0 \times 10^1$ | $0 \times 10^1$ |
| S. marcescens | $0 \times 10^1$ | $0 \times 10^1$ | $0 \times 10^1$ | $0 \times 10^1$ | $0 \times 10^1$ |
| P. cepacia | $34 \times 10^1$ | $0 \times 10^1$ | $0 \times 10^1$ | $0 \times 10^1$ | $0 \times 10^1$ |
| A. niger | $98 \times 10^3$ | $32 \times 10^3$ | $1 \times 10^1$ | $0 \times 10^1$ | $0 \times 10^1$ |
| P. aeruginosa | $0 \times 10^1$ | $0 \times 10^1$ | $0 \times 10^1$ | $0 \times 10^1$ | $0 \times 10^1$ |

TABLE IV

Solution B

| Organism | Viability (cfu/ml) | | | | |
|---|---|---|---|---|---|
| | 6 Hr | 1 day | 7 Day | 16 Day | 28 Day |
| S. aureus | $340 \times 10^3$ | $0 \times 10^1$ | $0 \times 10^1$ | $0 \times 10^1$ | $0 \times 10^1$ |
| ad. S. marcescens | $320 \times 10^3$ | $1232 \times 10^3$ | TNTC | TNTC | TNTC |
| S. marcescens | $0 \times 10^1$ | $0 \times 10^1$ | $0 \times 10^1$ | $0 \times 10^1$ | $0 \times 10^1$ |

TABLE IV-continued

Solution B

Viability (cfu/ml)

| Organism | 6 Hr | 1 day | 7 Day | 16 Day | 28 Day |
|---|---|---|---|---|---|
| P. cepacia | $868 \times 10^3$ | $1200 \times 10^3$ | TNTC | TNTC | TNTC |
| A. niger | $148 \times 10^3$ | $132 \times 10^3$ | $12 \times 10^3$ | $16 \times 10^1$ | $0 \times 10^1$ |
| P. aeruginosa | $0 \times 10^1$ | $0 \times 10^1$ | $0 \times 10^1$ | $0 \times 10^1$ | $0 \times 10^1$ |

TABLE V

Solution C

Viability (cfu/ml)

| Organism | 6 Hr | 1 day | 7 Day | 16 Day | 28 Day |
|---|---|---|---|---|---|
| S. aureus | $0 \times 10^1$ | $0 \times 10^1$ | $0 \times 10^1$ | $0 \times 10^1$ | $0 \times 10^1$ |
| ad. S. marcescens | $0 \times 10^1$ | $0 \times 10^1$ | $0 \times 10^1$ | $0 \times 10^1$ | $0 \times 10^1$ |
| S. marcescens | $0 \times 10^1$ | $0 \times 10^1$ | $0 \times 10^1$ | $0 \times 10^1$ | $0 \times 10^1$ |
| P. cepacia | $0 \times 10^1$ | $0 \times 10^1$ | $0 \times 10^1$ | $0 \times 10^1$ | $0 \times 10^1$ |
| A. niger | $143 \times 10^3$ | $146 \times 10^3$ | $95 \times 10^3$ | $21 \times 10^3$ | $.4 \times 10^3$ |
| P. aeruginosa | $0 \times 10^1$ | $0 \times 10^1$ | $0 \times 10^1$ | $0 \times 10^1$ | $0 \times 10^1$ |

EXAMPLE 2

Each of Solutions A, B and C from Example 1 was subjected to the following experiments to determine potential eye irritation of the solutions. The experimental methods follow the procedure developed by R. Tchao, which is described in "Trans-Epithelial Permeability of Fluorescein In Vitro as an Assay to Determine Eye Irritants", Progress in In Vitro Toxicology, Volume 6, 1988, pages 271–283 (Mary ann Liebert, Inc. Publishers, New York), the disclosure of which is incorporated herein by reference. The Tchao technique is described as a method of determining potential eye irritation of a substance by correlating damage to a monolayer of Madin-Darby Canine Kidney (MDCK) cells with damage to corneal epithelial cells.

Monolayer cultures of MDCK cells were grown on a filter membrane. The growth medium was removed and the cells were rinsed with Hanks Balanced Salt Solution (HBSS). Aliquots of Solutions A, B and C were applied to the obtained cell monolayers, incubated for 60 minutes, and then the test samples were removed and the cells were rinsed with HBSS. As a control, HBSS was applied to a cell monolayer in place of the test solutions. A sodium fluorescein solution was then applied to each cell monolayer for 30 minutes. Subsequently, the amount of fluorescein passing through the monolayer is quantified by fluorescence spectroscopy. The results are summarized in Table VI.

The amount of fluorescein passing through the cell monolayer is a function of permeability of the cell monolayer. Higher cell monolayer permeability indicates greater damage to the cell junctions from application of a test solution thereto, whereas lower cell monolayer permeability indicates less severe damage to the cell junctions from application of the test solution.

TABLE VI

| Test Sample | Fluorescence Units |
|---|---|
| Control | 55 (±7) |
| Solution A | 67 (±12) |

TABLE VI-continued

| Test Sample | Fluorescence Units |
|---|---|
| Solution B | 73 (±1) |
| Solution C | 134 (±11) |

The data summarized in Tables III, IV and V demonstrates that the solution of this invention (Solution A) provided a broader spectrum of antimicrobial efficacy than either of the comparative formulations (Solutions B and C). Additionally, the improved efficacy was achieved despite using lower amounts of the individual agents, i.e., the subject solution contained 0.0030 weight % chlorhexidine gluconate versus 0.0060 weight % chlorhexidine gluconate in Solution B, and 0.0005 weight % polyhexamethylene biguanide versus 0.0015 weight % polyhexamethylene biguanide in Solution C.

The improved efficacy for Solution A was especially significant when compared with Solution B. While the improvement in efficacy was less significant when compared with Solution C, the data summarized in Table VI demonstrates that Solution A exhibited significantly less potential for eye irritation than Solution C.

EXAMPLE 3

Various preservative systems were employed in saline solution buffered with a phosphate buffer. The resultant six solutions contained the antimicrobial agents shown in Table VII, noting that various solutions also contained disodium edetate as a sequestering agent. Each of the six solutions was subjected to challenge tests, wherein samples of each solution were inoculated with the organisms at the concentrations shown in Table VIII. Viability was tested at various periods following initial inoculation as reported in Tables IX, X, XI, XII, XIII and XIV.

TABLE VII

| Component | Solution | | | | | |
|---|---|---|---|---|---|---|
| | D | E | F | G | H | J |
| CHG* (Wt. %) | — | 0.0030 | 0.0030 | — | 0.0030 | 0.0030 |
| PHMB HCl** (Wt. %) | 0.0005 | — | 0.0005 | 0.0005 | — | 0.0005 |
| Na$_2$ EDTA*** (Wt. %) | — | — | — | 0.050 | 0.050 | 0.050 |

*Chlorhexidine Gluconate
**Polyhexamethylene Biguanide Hydrochloride (Cosmocil CQ)
***Disodium Edetate

TABLE VIII

| Organism | Inoculum (cfu/ml) |
|---|---|
| Pseudomonas aeruginosa 9027 | $3.9 \times 10^6$ |
| Staphylococcus aureus 6538 | $1.4 \times 10^6$ |
| Aspergillus niger | $2.9 \times 10^5$ |
| Candida albicans | $6.0 \times 10^5$ |
| adapted Serratia marcescens 48 | $3.8 \times 10^6$ |
| Serratia marcescens 48 | $2.4 \times 10^6$ |

TABLE IX

Solution D

| Orangism | Viability (cfu/ml) | | | | | | |
|---|---|---|---|---|---|---|---|
| | 6 Hr | 1 day | 2 Day | 7 Day | 14 Day | 21 Day | 28 Day |
| P. aerugiosa | $0 \times 10^1$ | $0 \times 10^1$ | $0 \times 10^1$ | $0 \times 10^1$ | $0 \times 10^1$ | $0 \times 10^1$ | $0 \times 10^1$ |
| S. aureus | $5 \times 10^1$ | $0 \times 10^1$ | $0 \times 10^1$ | $0 \times 10^1$ | $0 \times 10^1$ | $0 \times 10^1$ | $0 \times 10^1$ |
| A. niger | $133 \times 10^3$ | $186 \times 10^3$ | $183 \times 10^3$ | $142 \times 10^3$ | $90 \times 10^3$ | $254 \times 10^3$ | $192 \times 10^3$ |
| C. albicans | $0 \times 10^1$ | $0 \times 10^1$ | $0 \times 10^1$ | $0 \times 10^1$ | $0 \times 10^1$ | $0 \times 10^1$ | $0 \times 10^1$ |
| S. marcescens | $0 \times 10^1$ | $1 \times 10^1$ | $0 \times 10^1$ | $0 \times 10^1$ | $0 \times 10^1$ | $0 \times 10^1$ | $0 \times 10^1$ |
| ad S. marcescens | $270 \times 10^3$ | $19 \times 10^1$ | $1 \times 10^1$ | $0 \times 10^1$ | $468 \times 10^1$ | $3 \times 10^1$ | $27 \times 10^1$ |

TABLE X

Solution E

| Orangism | Viability (cfu/ml) | | | | | | |
|---|---|---|---|---|---|---|---|
| | 6 Hr | 1 day | 2 Day | 7 Day | 14 Day | 21 Day | 28 Day |
| P. aerugiosa | $0 \times 10^1$ | $0 \times 10^1$ | $0 \times 10^1$ | $0 \times 10^1$ | $0 \times 10^1$ | $0 \times 10^1$ | $0 \times 10^1$ |
| S. aureus | $95 \times 10^3$ | $4 \times 10^3$ | $0 \times 10^1$ | $0 \times 10^1$ | $0 \times 10^1$ | $0 \times 10^1$ | $0 \times 10^1$ |
| A. niger | $72 \times 10^3$ | $168 \times 10^3$ | $87 \times 10^3$ | $9 \times 10^3$ | $1 \times 10^3$ | $0 \times 10^1$ | $2 \times 10^1$ |
| C. albicans | $4 \times 10^1$ | $1 \times 10^1$ | $0 \times 10^1$ | $0 \times 10^1$ | $0 \times 10^1$ | $0 \times 10^1$ | $0 \times 10^1$ |
| S. marcescens | $12 \times 10^1$ | $0 \times 10^1$ | $0 \times 10^1$ | $0 \times 10^1$ | $0 \times 10^1$ | $0 \times 10^1$ | $0 \times 10^1$ |
| ad S. marcescens | $624 \times 10^3$ | $57 \times 10^3$ | $4 \times 10^3$ | $0 \times 10^1$ | $0 \times 10^1$ | $0 \times 10^1$ | $0 \times 10^1$ |

TABLE XI

Solution F

| Orangism | Viability (cfu/ml) | | | | | | |
|---|---|---|---|---|---|---|---|
| | 6 Hr | 1 day | 2 Day | 7 Day | 14 Day | 21 Day | 28 Day |
| P. aerugiosa | $0 \times 10^1$ | $0 \times 10^1$ | $0 \times 10^1$ | $0 \times 10^1$ | $0 \times 10^1$ | $0 \times 10^1$ | $0 \times 10^1$ |
| S. aureus | $0 \times 10^1$ | $0 \times 10^1$ | $0 \times 10^1$ | $0 \times 10^1$ | $0 \times 10^1$ | $0 \times 10^1$ | $0 \times 10^1$ |
| A. niger | $213 \times 10^3$ | $327 \times 10^3$ | $126 \times 10^3$ | $134 \times 10^3$ | $3 \times 10^1$ | $2 \times 10^1$ | $1 \times 10^1$ |
| C. albicans | $1 \times 10^1$ | $0 \times 10^1$ | $0 \times 10^1$ | $0 \times 10^1$ | $0 \times 10^1$ | $0 \times 10^1$ | $0 \times 10^1$ |
| S. marcescens | $0 \times 10^1$ | $0 \times 10^1$ | $0 \times 10^1$ | $0 \times 10^1$ | $0 \times 10^1$ | $0 \times 10^1$ | $0 \times 10^1$ |
| ad S. marcescens | $62 \times 10^1$ | $0 \times 10^1$ | $0 \times 10^1$ | $0 \times 10^1$ | $0 \times 10^1$ | $0 \times 10^1$ | $0 \times 10^1$ |

TABLE XII

Solution G

| Orangism | Viability (cfu/ml) | | | | | | |
|---|---|---|---|---|---|---|---|
| | 6 Hr | 1 day | 2 Day | 7 Day | 14 Day | 21 Day | 28 Day |
| P. aerugiosa | $0 \times 10^1$ | $0 \times 10^1$ | $0 \times 10^1$ | $0 \times 10^1$ | $0 \times 10^1$ | $0 \times 10^1$ | $0 \times 10^1$ |
| S. aureus | $6 \times 10^1$ | $0 \times 10^1$ | $0 \times 10^1$ | $0 \times 10^1$ | $0 \times 10^1$ | $0 \times 10^1$ | $0 \times 10^1$ |

TABLE XII-continued

Solution G

Viability (cfu/ml)

| Oragnism | 6 Hr | 1 day | 2 Day | 7 Day | 14 Day | 21 Day | 28 Day |
|---|---|---|---|---|---|---|---|
| A. niger | $250 \times 10^3$ | $266 \times 10^3$ | $184 \times 10^3$ | $136 \times 10^3$ | $126 \times 10^3$ | $131 \times 10^3$ | $221 \times 10^3$ |
| C. albicans | $0 \times 10^1$ | $0 \times 10^1$ | $0 \times 10^1$ | $0 \times 10^1$ | $0 \times 10^1$ | $0 \times 10^1$ | $0 \times 10^1$ |
| S. marcescens | $0 \times 10^1$ | $1 \times 10^1$ | $0 \times 10^1$ | $0 \times 10^1$ | $0 \times 10^1$ | $0 \times 10^1$ | $0 \times 10^1$ |
| ad S. marcescens | $700 \times 10^1$ | $10 \times 10^1$ | $22 \times 10^1$ | $0 \times 10^1$ | $0 \times 10^1$ | $0 \times 10^1$ | $0 \times 10^1$ |

TABLE XIII

Solution H

Viability (cfu/ml)

| Oragnism | 6 Hr | 1 day | 2 Day | 7 Day | 14 Day | 21 Day | 28 Day |
|---|---|---|---|---|---|---|---|
| P. aerugiosa | $0 \times 10^1$ | $0 \times 10^1$ | $0 \times 10^1$ | $0 \times 10^1$ | $0 \times 10^1$ | $0 \times 10^1$ | $0 \times 10^1$ |
| S. aureus | $258 \times 10^3$ | $0 \times 10^1$ | $0 \times 10^1$ | $0 \times 10^1$ | $0 \times 10^1$ | $0 \times 10^1$ | $0 \times 10^1$ |
| A. niger | $134 \times 10^3$ | $144 \times 10^3$ | $122 \times 10^3$ | $18 \times 10^3$ | $3 \times 10^3$ | $0 \times 10^1$ | $0 \times 10^1$ |
| C. albicans | $181 \times 10^3$ | $10 \times 10^1$ | $5 \times 10^1$ | $0 \times 10^1$ | $0 \times 10^1$ | $0 \times 10^1$ | $0 \times 10^1$ |
| S. marcescens | $2 \times 10^1$ | $0 \times 10^1$ | $0 \times 10^1$ | $0 \times 10^1$ | $0 \times 10^1$ | $0 \times 10^1$ | $0 \times 10^1$ |
| ad S. marcescens | $640 \times 10^3$ | TNTC | TNTC | TNTC | TNTC | $78 \times 10^1$ | $0 \times 10^1$ |

TABLE XIV

Solution J

Viability (cfu/ml)

| Oragnism | 6 Hr | 1 day | 2 Day | 7 Day | 14 Day | 21 Day | 28 Day |
|---|---|---|---|---|---|---|---|
| P. aerugiosa | $0 \times 10^1$ | $0 \times 10^1$ | $0 \times 10^1$ | $0 \times 10^1$ | $0 \times 10^1$ | $0 \times 10^1$ | $0 \times 10^1$ |
| S. aureus | $0 \times 10^1$ | $0 \times 10^1$ | $0 \times 10^1$ | $0 \times 10^1$ | $0 \times 10^1$ | $0 \times 10^1$ | $0 \times 10^1$ |
| A. niger | $78 \times 10^3$ | $150 \times 10^3$ | $191 \times 10^3$ | $13 \times 10^3$ | $4 \times 10^1$ | $2 \times 10^1$ | $0 \times 10^1$ |
| C. albicans | $1 \times 10^1$ | $0 \times 10^1$ | $0 \times 10^1$ | $0 \times 10^1$ | $0 \times 10^1$ | $0 \times 10^1$ | $0 \times 10^1$ |
| S. marcescens | $0 \times 10^1$ | $0 \times 10^1$ | $0 \times 10^1$ | $0 \times 10^1$ | $0 \times 10^1$ | $0 \times 10^1$ | $0 \times 10^1$ |
| ad S. marcescens | $35 \times 10^1$ | $0 \times 10^1$ | $0 \times 10^1$ | $0 \times 10^1$ | $0 \times 10^1$ | $0 \times 10^1$ | $0 \times 10^1$ |

Although certain preferred embodiments have been described, it is understood that the invention is not limited thereto and modifications and variations would be evident to a person of ordinary skill in the art.

We claim:

1. An ophthalmic solution comprising an antimicrobially effective amount of a preservative, wherein the preservative comprises: (a) chlorhexidine or a water-soluble salt thereof; and (b) polyhexamethylene biguanide or a water-soluble salt thereof.

2. The solution of claim 1, wherein component (a) is a water-soluble salt of chlorhexidine.

3. The solution of claim 2, wherein component (a) is chlorhexidine gluconate.

4. The solution of claim 1, wherein component (b) is a water-soluble salt of polyhexamethylene biguanide.

5. The solution of claim 4, wherein component (b) is polyhexamethylene biguanide hydrochloride.

6. The solution of claim 3, wherein component (b) is polyhexamethylene biguanide hydrochloride.

7. An aqueous solution for treating contact lenses comprising:

(a) about 0.0005 to about 0.0060 weight percent of chlorhexidine or a water-soluble salt thereof; and (b) about 0.00001 to about 0.0015 to weight percent of polyhexamethylene biguanide or a water-soluble salt thereof.

8. The solution of claim 7, Wherein component (a) is chlorhexidine gluconate and component (b) is hexamethylene biguanide hydrochloride.

9. The solution of claim 7, wherein component (a) is present at about 0.0020 to about 0.0040 weight percent and component (b) is present at about 0.0001 to about 0.0010 weight percent.

10. The solution of claim 9, wherein component (a) is present at about 0.0030 weight percent and component (b) is present at about 0.0005 weight percent.

11. The solution of claim 7, further comprising about 0.01 to about 2.5 weight percent of at least one buffering agent.

12. The solution of claim 7, further comprising about 0.025 to about 2.0 weight percent of ethylenediaminetetraacetic acid or a salt thereof.

13. The solution of claim 12, further comprising about 0.025 to about 2.0 weight percent of sodium edetate.

14. The solution of claim 7, further comprising at least one viscosity modifier.

15. The solution of claim 7, further comprising at least one wetting agent.

16. A method of treating a contact lens which comprises treating the lens with an aqueous solution comprising an antimicrobially effective amount of:

(a) chlorhexidine or a water-soluble salt thereof; and (b) polyhexamethylene biguanide or a water-soluble salt thereof.

17. The method of claim 16, wherein component (a) is a water-soluble salt of chlorhexidine and component (b) is a water-soluble salt of polyhexamethylene biguanide.

18. The method of claim 17, wherein component (a) is chlorhexidine gluconate and component (b) is polyhexamethylene biguanide hydrochloride.

19. The method of claim 14, wherein the solution comprises:
   (a) about 0.0005 to about 0.0060 weight percent of chlorhexidine or a water-soluble salt thereof; and
   (b) about 0.00001 to about 0.0015 to weight percent of polyhexamethylene biguanide or a water-soluble salt thereof.

20. The method of claim 19, wherein component (a) is present at about 0.0020 to about 0.0040 weight percent and component (b) is present at about 0.0001 to about 0.0010 weight percent.

21. A method of preserving an ophthalmic solution which comprises including in the solution an antimicrobially effective amount of a preservative system consisting essentially of:
   (a) chlorhexidine gluconate; and
   (b) polyhexamethylene biguanide hydrochloride.

22. The method of claim 21, wherein the solution includes disodium edetate.

* * * * *

UNITED STATES PATENT AND TRADEMARK OFFICE
CERTIFICATE OF CORRECTION

PATENT NO. : 5,453,435
DATED : September 26, 1995
INVENTOR(S) : Manohar K. Raheja, et. al.

It is certified that error appears in the above-indentified patent and that said Letters Patent is hereby corrected as shown below:

In column 4, line 39, replace "cedacia" with -- cepacia --.

In Columns 7 and 8, in the last line of Table IX, under the heading "6 Hr", change "270 x $10^3$" to -- 170 x $10^1$ --.

In Columns 7 and 8, in the third line of Table XI, under the heading "1 day", change "327 x $10^3$" to -- 227 x $10^3$ --.

Signed and Sealed this

Second Day of July, 1996

*Attest:*

BRUCE LEHMAN

*Attesting Officer*     Commissioner of Patents and Trademarks